United States Patent [19]

Enfors et al.

[11] 4,346,175

[45] Aug. 24, 1982

[54] PROCESS FOR THE MICROBIOLOGICAL MODIFICATION OF HARDWOOD BY THE ACTION OF MICROORGANISMS

[75] Inventors: Sven-Olof Enfors, Mellanvägen 4, Stanstorp, S-243 00 Höör; Nils Molin, Clementstorget 12, S-222 Lund; Eugen Montelin, Majorsgatan 41, S-290 Ahus, all of Sweden

[73] Assignees: Sven-Olof Enfors, Hoor; Nils Molin, Lund; Eugen Montelin, Ahus, all of Sweden

[21] Appl. No.: 948,275

[22] Filed: Oct. 3, 1978

[30] Foreign Application Priority Data

Oct. 4, 1977 [SE] Sweden ............................... 7711089

[51] Int. Cl.$^3$ ................................................ C12P 1/02

[52] U.S. Cl. .................................... 435/317; 435/262; 435/274; 435/277; 435/171; 435/838; 435/911

[58] Field of Search ..................... 195/1, 8, 9, 10, 104, 195/33; 435/262, 267, 274, 278, 317, 277

[56] References Cited

U.S. PATENT DOCUMENTS

| | | | |
|---|---|---|---|
| 1,380,354 | 6/1921 | Carpenter | 195/8 |
| 2,617,202 | 11/1952 | Reedy | 34/13.8 |
| 2,643,957 | 6/1953 | Lindgren | 195/8 X |
| 3,486,969 | 12/1969 | Nilsson et al. | 195/10 |
| 3,962,033 | 6/1976 | Eriksson et al. | 195/8 |

FOREIGN PATENT DOCUMENTS 24595 of 1913 United Kingdom .

*Primary Examiner*—Lionel M. Shapiro

*Attorney, Agent, or Firm*—Beveridge, DeGrandi, Kline and Lunsford

[57] ABSTRACT

The disclosure relates to a process for the microbiological modification of hardwood in that a microorganism, or an enzymatically active preparation thereof, specially selected for the hardwood in question, is supplied to the surface of the wood for attack thereof under carefully regulated conditions as regards temperature, relative moisture content, $O_2$ content and $CO_2$ content. Thereafter, the process is discontinued in a suitable manner, for example by treatment with steam or hot water, followed by drying; or by drying only.

14 Claims, No Drawings

PROCESS FOR THE MICROBIOLOGICAL MODIFICATION OF HARDWOOD BY THE ACTION OF MICROORGANISMS

The present invention relates to a process for the microbiological degradation of hardwood by the action of microorganisms.

In nature, a continuous degradation of wood takes place by attack by microorganisms, an industrially worthless wood product being formed. However, studies have shown that a suitable control of this natural degradation results in a wood product of high porosity and low weight which makes the wood product usable as a raw material in different industrial fields of use. In certain cases, the thus formed product is even better than normal wood which has not been attacked.

On the basis of this insight a controlled process has been developed by a series of experiments in which fungi related to white rot fungi, for example Pleurotus ostreatus and Trametes versicolor are allowed, after inoculation into hardwood, in particular beech, to attack the wood for varying periods of time and under controlled temperature and moisture content in the hardwood, with a resultant wood product which is advantageous in many respects. The thus obtained wood product is known as "Mykoholz" and has proved, thanks to its ease of processing and light weight, to be suitable as a starting material for the manufacture of int. al. lead pencils. Moreover, because of its high porosity, this wood product is capable of rapidly absorbing water by suction and leading off water vapour, which has made the wood product usable as a starting material for wooden molds in the glass manufacture industry.

Apart from the above-disclosed fields of application, the controlled fungus-attacked wooden product (Mykoholz) has several other fields of use such as in the manufacture of furniture and as fire protection material after impregnation. Thus, this product may be utilized in many diversified fields.

One disadvantage in the prior art process is that it is far too time-consuming (several weeks) and thereby unsuited for industrial exploitation on a large scale. Moreover, the process is restricted to the exclusive utilization of fungi related to the white rot fungus group.

The object of the present invention is to realize an industrially applicable process for the rapid microbiological modification of hardwood for the production of a versatile wood product by the action of microorganisms, whereby the disadvantages inherent in the prior art process are obviated.

A further object of the present invention is to realize a process for the microbiological modification of hardwood by the action of microorganisms, the process not being restricted to the exclusive use of fungi related to the white rot fungus group, but being extended such that fungi, bacteria and enzymatically active preparations thereof may also be used.

According to the present invention, a hardwood which is to be subjected to microbiological modification is implanted with a specially selected microorganism as such or in the form of an enzymatically active preparation thereof, in a sufficient amount in or on the surface of the wood for attack thereof, at the same time as temperature, relative moisture content in the wood, $O_2$ content and $CO_2$ content are carefully regulated with respect to the selected microorganism or enzymatically active preparation thereof so that a desired modification of the hardwood is achieved. The microbiological process is thereafter discontinued in a suitable manner. Such a suitable manner includes treatment with steam or hot water, followed by drying; or simply drying.

The hardwood is implanted with the microorganism preferably by inoculation with a spore preparation, mycelium, infected sawdust or other carrier material treated with the microorganism or its enzymatically active preparation.

In order to reduce the amount of natural microorganisms which may lead to an uncontrolled modification of the wood, the wood may, prior to inoculation, be treated, for example by sterilization or disinfection.

The wood may be pretreated with steam and/or growth-regulating substances for the selected microorganisms. The wood may also be pretreated with enzymatically active preparations. As enzymatically active preparations there may be selected, for example, pectinase and/or cellulase.

The hardwoods which are selected according to a preferred embodiment of the invention are beech, alder or birch, for example in the form of veneer.

Preferred microorganisms are such as produce a color pigment which is fixed in the wood structure, stimulate the release of the natural resins and vegetable gums of the wood or which give rise to acidic substance reaction and degradation products. These latter microorganisms produce different degrees of acidity in different portions, which results in different color intensities in different portions of the wood.

According to a further preferred embodiment of the invention, the degradation is controlled in such a manner that microbiologically modified portions of the wood alternate with untreated portions, for example by drying or by the addition of poisons. Hereby, a product of dimensional stability will be obtained with portions at different levels of hardness.

The Table below provides a survey of the concrete embodiments of the invention with specific regions for the selected microorganism as regards temperature, relative moisture content, $O_2$ content and $CO_2$ content in the microbiological degradation of hardwood.

| Example No. | Hardwood | Microorganism | Temperature °C. | Relative moisture content, % | $O_2$ content % | $CO_2$ content % |
|---|---|---|---|---|---|---|
| 1 | beech,birch alder | *Armillaria mellea* | 15–40 | 30–90 | about 20–21 | up to about 5 |
| 2 | beech,birch alder | *Xylaria polymorfa* | 13–40 | 35–80 | about 20–21 | up to 5 |
| 3 | beech,birch alder | *Bacillus polymyxa* | 20–35 | 80–100 | up to 21 | 5 |

The process according to the invention will realize a microbiologically modified wood of high porosity, whereby penetration of substances which are added in order to provide the desired color and hardness will be facilitated. The product may also be impregnated with, for example, silicic acid derivatives which give increased fire-resistance and improved acoustic properties in the wood.

The process according to the invention permits of a rapid and controlled microbiological modification of hardwood, as opposed to the slow and uncontrolled process cycles in nature. Moreover, the present invention provides a modification process which, in relation to the prior art, is more rapid, economically viable and industrially acceptable on a large scale.

In utilization of hardwood in the form of veneer, a product will be obtained according to the invention which is of great technical interest and may be used for veneered products. Special mention might be made of the manufacture of loud-speaker boxes.

What we claim and desire to secure by Letters Patent is:

1. A process for the controlled microbiological modification of hardwood to produce a wood product of high porosity by the action of microorganisms, wherein an aerobic microorganism selected from the group consisting of *Armillaria mellea, Xylaria polymorpha, Bacillus polymyxa,* and an enzymatically active preparation thereof, specially selected for the hardwood in question, is implanted in a sufficient amount in or on the surface of the wood for attack thereof, and wherein the temperature moisture content in the wood, $O_2$ content and $CO_2$ content are adjusted in relation to the selected microorganism or enzymatically active preparation thereof, selective modification of the hardwood being thereby realized, and wherein the process is discontinued in a suitable manner.

2. The process of claim 1, wherein the fungus Armillaria mellea is selected as the microorganism, and wherein the temperature is adjusted to from 20° to 40° C., the relative moisture content in the wood to from 30 to 90% and the $O_2$ content and $CO_2$ content to approximately 20 to 21% and up to 5%, respectively.

3. The process of claim 1, wherein Xylaria polymorfa is selected as the microorganism, and wherein the temperature is adjusted to from 13° to 40° C., the relative moisture content in the wood to from 35 to 80%, and the $O_2$ content and $CO_2$ content to from 20 to 21% and up to 5%, respectively.

4. The process of claim 1, wherein Bacillus polymyxa is selected as the microorganism, and wherein the temperature is adjusted to from 20° to 35° C., the relative moisture content in the wood to from 80 to 100% and the $O_2$ content and $CO_2$ content to up to 21% and 5%, respectively.

5. The process of claim 1, wherein pectinase and/or cellulase are selected as the enzymatically active preparation.

6. The process of claim 1, wherein the wood is pretreated with steam and/or growth substances for the microorganism.

7. The process of claim 1, wherein the wood is inoculated with a spore preparation, mycelium, infected sawdust or other carrier material treated with microorganism.

8. The process of claim 1, wherein the process is discontinued by treatment with steam or hot water, followed by drying; or by drying only.

9. The process of claim 1, wherein hardwood in the form of veneer is utilized.

10. The process of claim 1, wherein the hardwood is selected from the group comprising beech, alder and birch.

11. The process of claim 1, wherein an organism producing a color pigment which is fixed in the wood structure is selected as microorganism.

12. The process of claim 1, wherein an organism stimulating the release of the natural resins and vegetable gums of the wood is selected as microorganism.

13. The process of claim 1, wherein the degradation is controlled in such a manner that a mosaic of microbiologically modified and untreated portions is obtained.

14. The process of claim 1, wherein an organism which gives rise to acidic substance reaction and degradation products is selected as microorganism.

* * * * *